United States Patent [19]
Burke

[11] Patent Number: 5,817,343
[45] Date of Patent: Oct. 6, 1998

[54] METHOD FOR FABRICATING POLYMER-BASED CONTROLLED-RELEASE DEVICES

[75] Inventor: Paul A. Burke, Medford, Mass.

[73] Assignee: Alkermes, Inc., Cambridge, Mass.

[21] Appl. No.: 649,128

[22] Filed: May 14, 1996

[51] Int. Cl.[6] .................................................. A61K 9/14
[52] U.S. Cl. ......................... 424/489; 514/951; 424/426
[58] Field of Search ..................................... 424/486, 489

[56] References Cited

U.S. PATENT DOCUMENTS

| | | | |
|---|---|---|---|
| 4,293,539 | 10/1981 | Ludwig et al. | 424/19 |
| 4,703,008 | 10/1987 | Lin | 435/240.2 |
| 4,818,542 | 4/1989 | DeLuca et al. | 424/491 |
| 5,019,400 | 5/1991 | Gombotz et al. | 424/497 |
| 5,192,741 | 3/1993 | Orsolini et al. | 514/4 |
| 5,384,124 | 1/1995 | Courteille et al. | 424/486 |
| 5,401,502 | 3/1995 | Wunderlich et al. | 424/486 |
| 5,439,688 | 8/1995 | Orsolini et al. | 424/489 |
| 5,478,564 | 12/1995 | Wantier et al. | 424/486 |

OTHER PUBLICATIONS

Tabata, Y., et al., "A formulation method using D,L–lactic acid oligomer for protein release with reduced initial burst," *J. of Controlled Release*, 23: 55–64 (1993).
Wise, D.L., "Biopolymeric Controlled Release Systems", (vol. I), eds. *CRC Press Inc.*, Boca Raton, FL, pp. 115–181 (1984).
Allemann, E., et al., "Preparation of aqueous polymeric nanodispersions by a reversible salting–out process: influence of process parameters on particle size", *International J. of Pharmaceutics*, 87: 247–253 (1992).
Bodmeier, R. and Chen, H., "Preparation of Biodegradable Poly (+/−)lactide Microparticles Using a Spray–Drying Technique", *J. Pharm. Pharmacol.*, 40: 754–757 (1988).
Gangadharam, P.R., et al., "Sustained release of isoniazid in vivo from a single implant of a biodegradable polymer", *Tubercle*, 72: 115–122 (1991).
Kitchell, J. P. and Wise, D. L., "Poly(lactic/glycolic acid) biodegradable drug–polymer matrix systems", *Methods in Enzymology* 112: 436–448 (1985).
Langer, R. and Folkman, J., "Polymers for the sustained release of proteins and other macromolecules", *Nature*, 263: 797–800 (1976).

(List continued on next page.)

*Primary Examiner*—Peter F. Kulkosky
*Attorney, Agent, or Firm*—Hamilton, Brook, Smith & Reynolds, P.C.

[57] ABSTRACT

A method for forming polymer/drug microparticles comprising the steps of (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) fragmenting the polymer/drug matrix at a temperature below the glass transition temperature of the polymer/drug matrix, thereby forming polymer/drug matrix microparticles.

In one embodiment, the solvent is removed from a polymer solution/drug mixture by freezing the polymer solution/drug mixture and extracting the solvent from the resulting solid polymer solution/drug matrix. The polymer can be a biocompatible polymer, such as poly(lactic acid-co-glycolic acid). The drug can be a labile drug, such as a protein, or a polynucleotide. Another embodiment of the present invention includes the polymer/drug matrix microparticles which are formed by the method outlined above. A further embodiment of the present invention includes a method for producing an implantable polymer/drug matrix mass, comprising the steps of (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) mechanically compressing the polymer/drug matrix, thereby forming an implantable polymer/drug matrix mass.

33 Claims, 3 Drawing Sheets

OTHER PUBLICATIONS

Preis, I. and Langer, R. S., "A single–step immunization by sustained antigen release", *J. of Immunological Methods*, 28: 193–197 (1979).

Rhine, W. D., et al., "Polymers for Sustained Macromolecule Release: Procedures to Fabricate Reproducible Delivery Systems and Control Release Kinetics", *J. of Pharmaceutical Sciences*, 69(3): 265–270 (1980).

Sato, T., et al., "Porous biodegradable microspheres for controlled drug delivery I. Assessment of processing conditions and solvent removal techniques", *Pharmaceutical Research*, 5(1):21–30. (1988).

Schwope, A. D., et al., "Lactic/glycolic acid polymers as narcotic antagonist delivery systems", *Life Sciences*, 17: 1877–1886 (1975).

Tabata, Y., et al., "Injectable polyanhydride granules provide controlled release of water–soluble drugs with a reduced initial burst", *J. of Pharmaceutical Sciences*, 83(1): 5–11 (1994).

Wang, H. T., et al., "Degradation of poly(ester) microspheres", *Biomaterials*, 11: 679–685 (1990).

Wise, D. L. et al., "Long–term controlled delivery of levonorgestrel in rats by means of small biodegradable cylinders", *J. of Pharmacy and Pharmacology*, 32: 399–403 (1980).

Yolles, S., et al., "Controlled release of biologically active agents", *Controlled Release Polymeric Formulations*, New York, NY *American Cancer Society* (1976).

Anderson, L. C., et al., "An Injectable Sustained Release Fertility Control System", *Contraception* 13(3); 375–385 (1976).

Gould, L., et al., "Fifty:fifty poly (DL glycolic acid–lactic acid) copolymer as a drug delivery system for 5–fluorouracil: a histopathological evaluation", *Can J. Ophthalmol* 29(4): 168–171 (1994).

Siegel, R.A. and Langer, R., "Controlled Release of Polypeptides and Other Macromolecules", *Pharmaceutical Research* 2–10 (1984).

Langer, R., "[4] Polymers for the Sustained Release of Macromolecules: Their Use in a Single–Step Method of Immunization", *Methods in Enzymology* 73: 57–75 (1981).

Gresser, J. D., et al., "Larger Animal Testing of An Injectable Sustained Release Fertility Control System", *Contraception* 17(3): 253–266 (1978).

Jackanicz, T. M., et al., "Polylactic Acid As A Biodegradable Carrier for Contraceptive Steroids", *Contraception* 8(3): 227–234 (1973).

Wise, D. L., et al., "Sustained Release of an Antimalarial Drug Using a Copolymer of Glycolic/lactic acid", *Life Sciences* 19: 867–874 (1976).

METHOD FOR FABRICATING POLYMER-BASED CONTROLLED-RELEASE DEVICES

BACKGROUND OF THE INVENTION

An area of current research focus in the pharmaceutical industry is the development of methods for the controlled or sustained release of drugs. Such methods obviate certain problems associated with traditional methods for administering drugs, such as noncompliance of patients with a prescribed medication schedule, the need for multiple injections, and fluctuating concentrations of the drug in the body. These problems are particularly acute when the drug is a protein or peptide. Such drugs frequently have short in vivo half-lives. In addition, protein-based drugs cannot be administered orally in an unprotected state due to the rapid degradation that occurs in the digestive tract.

Methods for sustained or controlled drug release can utilize an implanted device, such as an osmotic pump, or a drug dispersed in a biocompatible polymer matrix, which can be implanted, administered orally or injected. Polymers often used in such applications include poly(lactic acid) and poly(lactic acid-co-glycolic acid). Both polymers undergo slow hydrolysis in vivo, releasing the entrapped drug. The polymer degradation products are the parent acids, which are absorbed by the body.

Polymer/drug matrix particles to be administered via injection must have a size range typically on the order of 200 microns or less. The size and morphology of polymer/drug matrix particles depends upon the fabrication method employed, and the formation of small polymer/drug matrix particles in which the drug is a protein is currently limited to a few techniques. For example, polymer/protein matrix particles comprising poly(lactic acid) and either trypsin or insulin, were prepared by both an oil/water emulsion method and a neat mixing method at elevated temperature (Tabata et al., *J. Cont. Release* 23: 55–64 (1993)). The polymer/protein matrices thus formed were subsequently ground into granules. The granules prepared by the neat mixing method lost a significant fraction (10%) of protein activity, possibly due to the heating step. These granules also suffered from a large initial burst of protein release. The granules prepared by the oil/water emulsion method lost an even greater amount (about 40–60%) of protein activity, possibly caused by protein lability with respect to the oil.

A method for forming injectable polymer/drug matrix microparticles was disclosed by Wise (Wise in *Biopolymeric Controlled Release Systems*, Vol.1, Wise, ed., CRC Press-:Boca Raton, Chapter 8 (1984)). Microparticles comprising poly(lactic acid-co-glycolic acid) and the narcotic antagonist naltrexone were formed by cryogenic grinding of beads or rods of a solid polymer/naltrexone matrix. The beads and rods were formed by molding a polymer/naltrexone matrix film into the desired shape at a temperature above the softening point of the polymer. Thus, this method is not suitable for the preparation of polymer/drug matrix microparticles incorporating a thermally labile drug, such as many proteins, peptides and polynucleotides and analogs.

Another example, disclosed in U.S. Pat. No. 5,019,400, issued to Gombotz et al., the contents of which are incorporated herein by reference, is a method for producing polymer/protein microspheres. This method involves atomizing a mixture comprising a biocompatible polymer and a drug substance, and freezing the resulting aerosol droplets. In this method, particle size and shape depend upon the method of atomization and the flow rate of the polymer solution through the atomizer. A number of variables are tightly controlled in order to optimize reproducibility in particle sizes and morphologies.

Current methods for the formation of polymer/drug matrix implants suffer from drawbacks when utilized with thermally labile or organic solvent labile drugs. These methods employ harsh conditions, such as elevated temperatures (greater than about 45° C.) and/or aqueous/organic emulsions, which can result in a significant loss of drug activity. Other methods utilize a simple mixture of bulk polymer with solid drug, which does not yield a fine microscopic dispersion of the drug within the polymer matrix, resulting in a more erratic drug release in vivo.

The need exists for a method for forming polymer/drug matrix devices suitable for injection or implantation in which the solid polymer/drug matrix is formed by methods suitable for thermally sensitive drugs, as well as drugs sensitive, under certain conditions, to organic solvents, while still achieving a substantially uniform distribution of the drug throughout the matrix. In addition, the method must be amenable to scale-up, and to performance in a closed, sanitized environment to enable the efficient, economical manufacture of polymer/drug matrix controlled release devices meeting FDA sterility requirements.

SUMMARY OF THE INVENTION

The present invention relates to a method for forming polymer-encapsulated drug microparticles (hereinafter referred to as "polymer/drug matrix microparticles"). The method comprises (1) forming a polymer solution/drug mixture comprising a polymer dissolved in an organic solvent and a co-dissolved or suspended drug; (2) removing the solvent from the polymer solution/drug mixture, thereby forming a solid polymer/drug matrix; and (3) fragmenting the polymer/drug matrix at a temperature below the glass transition temperature of the polymer/drug matrix, thereby forming polymer/drug matrix microparticles. The polymer/drug matrix can be fragmented by, for example, grinding or milling. In one embodiment, the polymer/drug matrix is formed by removing the solvent from a polymer solution/drug mixture, for example, by freezing the polymer solution/drug mixture and extracting the solvent from the resulting solid polymer solution/drug matrix.

In one embodiment, the polymer solution/drug mixture is frozen by, for example, pouring, dripping, atomizing or extruding the mixture into a liquid nonsolvent which is at a temperature below the freezing point of the polymer solution/drug mixture. The polymer can be any biocompatible polymer, such as poly(lactic acid) or a poly(lactic acid-co-glycolic acid) copolymer. The drug can be a therapeutic, prophylactic or diagnostic agent, such as a protein, nucleic acid or small organic molecule.

Another embodiment of the present invention includes the polymer/drug matrix particles that are formed by the method outlined above. Preferably, these particles are microparticles. These comprise a biocompatible polymer, such as poly(lactic acid) or a poly(lactic acid-co-glycolic acid) copolymer, a drug, such as a therapeutic, prophylactic or diagnostic agent, and, optionally, one or more excipients or release modifiers, such as a metal-containing salt.

A further embodiment of the present invention is a method for forming an implantable polymer/drug matrix mass. The method comprises the steps of (1) forming a polymer solution/drug mixture comprising a polymer dissolved in an organic solvent and a co-dissolved or suspended drug; (2) removing the solvent from the polymer solution/drug mixture, thereby forming a solid polymer/drug matrix;

and (3) mechanically compressing the polymer/drug matrix, thereby forming an implantable polymer/drug matrix mass. The invention also includes a implantable drug/polymer matrix mass produced by this method. The method, thus, produces a substantial dispersion of the drug substance throughout the polymer matrix without using heat extrusion.

The method described herein offers the advantage of uncoupling the polymer/drug matrix fabrication step from the fragmentation or compression step, which determines the polymer/drug matrix device size and morphology. The method allows the use of fabrication methods employing mild conditions, for example, low temperature. Thus, the method is particularly well-suited for thermally labile drugs, such as many proteins, polypeptides and polynucleotides. The method also enables the formation of the polymer/drug matrix without dissolving the drug in an organic solvent, or bringing an aqueous solution of the drug into contact with an organic solvent. Certain drugs, such as many proteins and oligonucleotides, are soluble in few organic: solvents suitable for forming polymer solutions, and are denatured at an aqueous/organic interface, a problem which is eliminated by the present invention. The method, thus, allows the formation of polymer/drug matrix microparticles and implantable devices maintaining a high degree (greater than about 90%) of the drug, for example, protein, activity present prior to processing.

The method also reduces process variables in the determination of particle size and allows for storage of the solid polymer/drug matrix prior to fragmentation or compression. These features provide considerably more flexibility and simplicity in the manufacture of polymer/drug matrix microparticles and implantable devices than provided by previously described methods and permit the facile scale-up of the method.

DETAILED DESCRIPTION OF THE INVENTION

Figure 1:
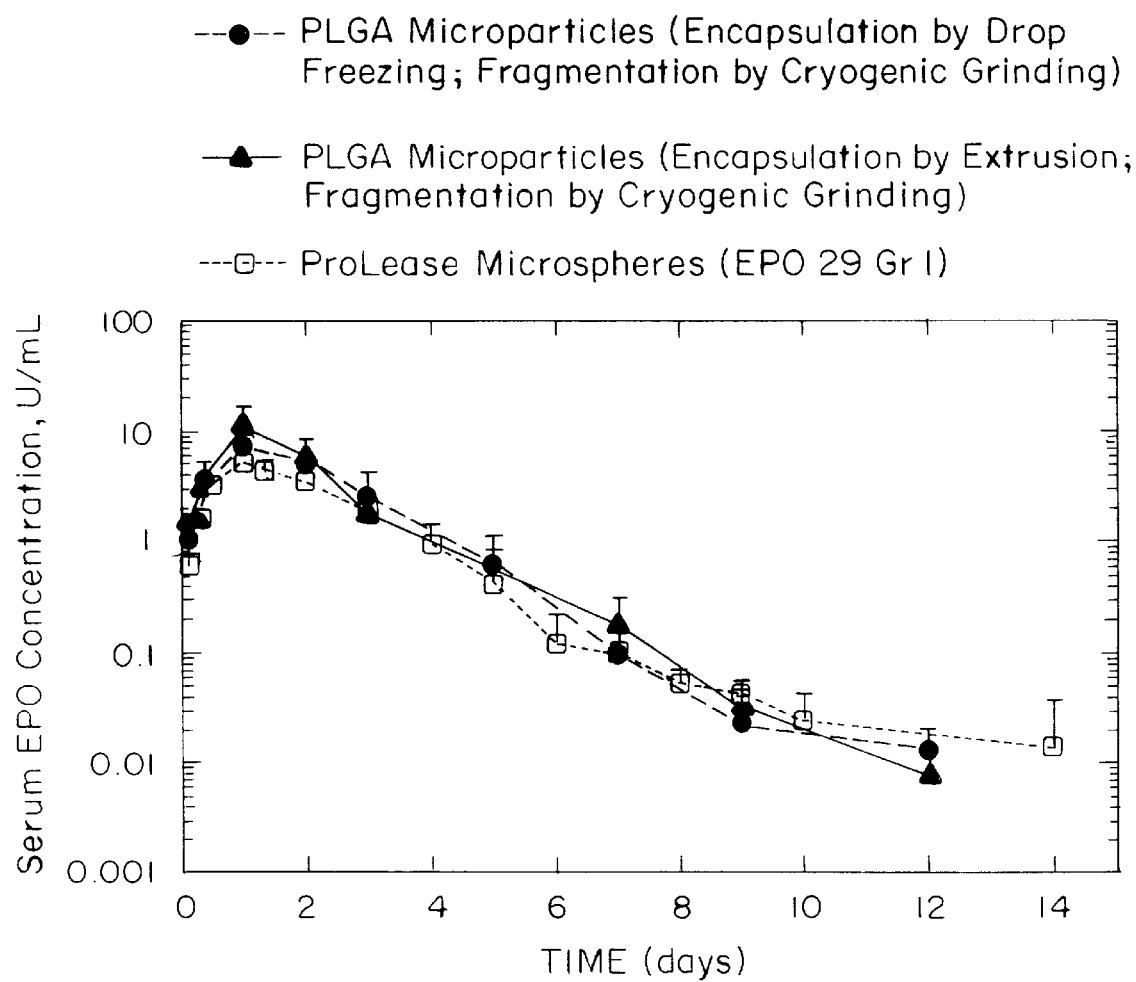
FIG. 1 is a graph comparing the in vivo release in rats of erythropoietin from poly(lactic acid-co-glycolic acid)/EPO microparticles produced by cryogenic grinding and from poly(lactic acid-co-glycolic acid)/EPO microspheres produced by the method described in U.S. Pat. No. 5,019,400, issued to Gombotz et al.
Figure 2:
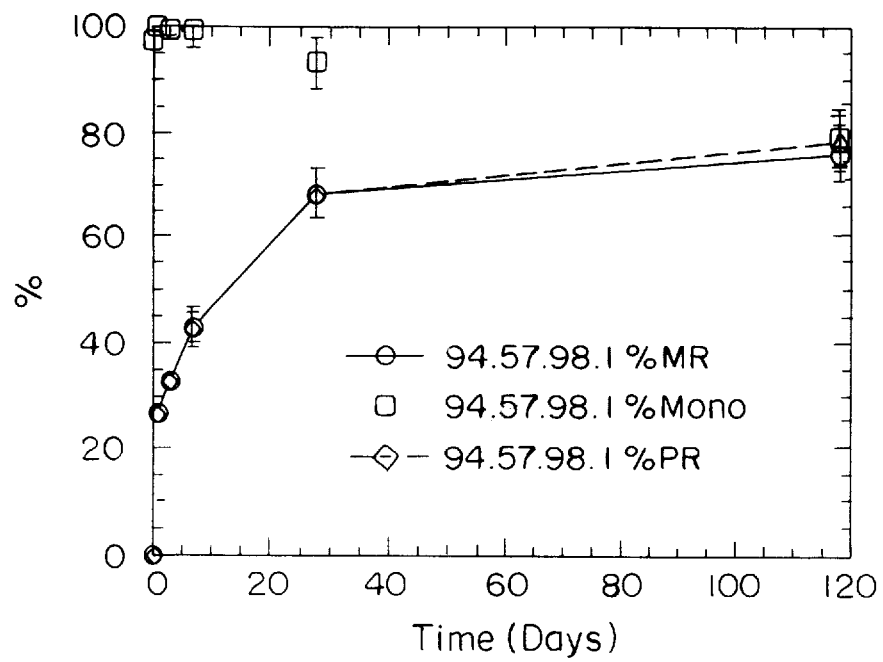
FIG. 2 is a graph showing in vitro release of EPO from poly(lactic acid-co-glycolic acid)/EPO microparticles prepared from a polymer/EPO matrix formed by drop freezing followed by solvent extraction.
Figure 3:
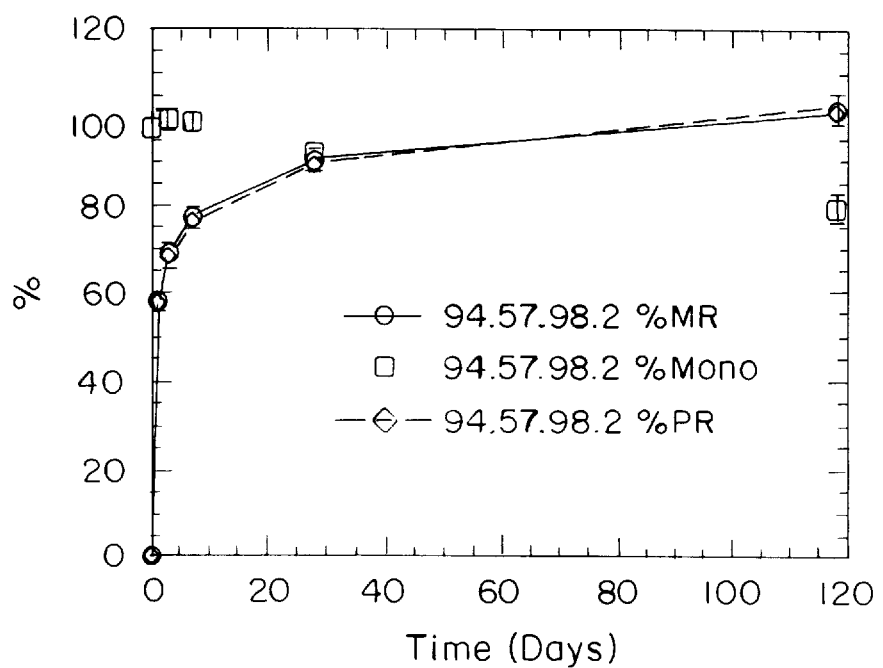
FIG. 3 is a graph showing in vitro release of EPO from poly(lactic acid-co-glycolic acid)/EPO microparticles prepared from a polymer/EPO matrix formed by extrusion into liquid nitrogen.

The present invention relates to a method for forming polymer-encapsulated drug microparticles (hereinafter referred to as "polymer/drug matrix microparticles"). The method comprises (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) fragmenting the polymer/drug matrix at a temperature below the glass transition temperature of the polymer/drug matrix, thereby forming polymer/protein matrix microparticles. The polymer/drug matrix can be fragmented by, for example, grinding or milling. In one embodiment, the solvent is removed from the polymer solution/drug mixture by freezing the polymer solution/drug mixture and extracting the solvent from the resulting solid polymer solution/drug matrix into a nonsolvent.

Another embodiment of the present invention includes the polymer/drug matrix particles that are formed by the method of the present invention. Preferably these particles are microparticles. These comprise a biocompatible polymer, such as poly(lactic acid) or a poly(lactic acid-co-glycolic acid) copolymer, a drug substance, and, optionally, one or more excipients and/or release modifiers, such as a metal-containing salt. The particles can further comprise one or more additional drugs.

An additional embodiment of the present invention is a method for fabricating biodegradable implants containing encapsulated labile drugs. The method comprises the steps of (1) forming a polymer solution/drug mixture comprising a polymer dissolved in an organic solvent and a co-dissolved or suspended drug; (2) removing the solvent from the polymer solution/drug mixture, thereby forming a solid polymer/drug matrix; and (3) mechanically compressing the polymer/drug matrix, thereby forming an implantable polymer/drug matrix mass.

The term "labile drug" as used herein refers to a drug which loses a substantial amount of activity when either warmed to elevated temperatures, such as temperatures greater than physiological temperatures (about 37° C.), or dissolved in an organic solvent or in solution at an aqueous/organic interface. In the former case, the drug can also be referred to as a "thermally labile drug", while in the latter case, the drug can additionally be referred to as an "organic solvent labile drug". Examples of labile drugs include proteins, polypeptides and polynucleotides. Molecules of these types often exist under physiological conditions in conformations essential to activity, and, upon warming, undergo a conformational change. The active conformations can be stabilized by interactions such as hydrogen bonds and salt bridges, which can be disrupted when the molecule is dissolved in a nonaqueous solvent, such as dimethylsulfoxide or 1,1,1,3,3,3-hexafluoroisopropanol, or is present at an aqueous/organic interface. The method of the present invention is particularly advantageous for labile drugs, because it enables low temperature, i.e., room temperature or below, formation of the polymer/drug matrix. In addition, the method enables the formation of the polymer/drug matrix without dissolving the drug in an organic solvent.

As used herein the term "drug" refers to an agent, or its pharmaceutically acceptable salt, which possesses therapeutic, prophylactic or diagnostic properties in vivo. Examples of suitable therapeutic or prophylactic agents which can be labile drugs include, for example, proteins such as immunoglobulin-like proteins, antibodies, cytokines (e.g., lymphokines, monokines, chemokines), interleukins, interferons, erythropoietin (also referred to herein as "EPO"), nucleases, tumor necrosis factor, colony stimulating factors, insulin, enzymes, tumor suppressors, hormones (e.g., growth hormone and adrenocorticotrophic hormone), antigens (e.g., bacterial and viral antigens), growth factors, peptides, polypeptides, and polynucleotides, such as antisense molecules.

The term "polymer/drug matrix", as used herein, refers to a solid material comprising a polymer, copolymer or polymer blend, and drug molecules, which are dispersed throughout the polymer matrix. The polymer/drug matrix can be homogeneous or heterogeneous, and can further comprise excipients, such as surfactants or sugars, release modifying agents, such as metal-containing salts, or one or more additional drug substances.

The term "nonsolvent", as used herein, refers to a material, which, in the liquid or solid state, does not substantially dissolve a second or reference material. Such a material can, thus, be described as a nonsolvent for the reference material.

The term "microparticle", as used herein, refers to a particle of any morphology which has a largest dimension of less than about 500 $\mu$m (e.g., has a largest dimension on the order of about $5\times10^{-4}$ m or less).

The term "release-modifying agent", as used herein, refers to a material which, when incorporated into a polymer/drug matrix, modifies the drug-release characteristics of the matrix. A release modifying agent can, for example, either decrease or increase the rate of drug release from the matrix. One group of release modifying agents includes metal-containing salts, as disclosed in U.S. patent application Ser. No. 08/237,057 by Bernstein, et al., the contents of which are incorporated herein by reference.

An advantage of the present invention is that the polymer/drug matrix can be formed from the polymer solution/drug mixture under mild conditions. The polymer solution/drug mixture comprises a biocompatible polymer dissolved in a solvent and a co-dissolved or suspended drug. If suspended, the drug can be present, for example, as a powder, which can be microcrystalline or partially amorphous. When the drug is suspended in the mixture, it can be dispersed substantially evenly throughout the mixture by agitation, for example by shaking, stirring, vortexing, homogenizing or sonicating. The weight of dissolved or suspended drug relative to the weight of dissolved polymer can range from about 0.02% to 100%. The polymer solution/drug mixture can further comprise one or more excipients, including sugars, acids, bases, surfactants and stabilizers and/or a release modifying agent, such as a metal-containing salt. The polymer solution/drug mixture can further comprise one or more additional drugs.

The solid polymer/drug matrix can be formed by any method which results in removal of the solvent from the polymer solution/drug mixture, thereby forming a solid mass of any geometry or size, throughout which the drug molecules and any excipient(s) and/or release modifiers are distributed. The method for forming the solid polymer/drug matrix should not substantially degrade the drug, and, for example, can be conducted at low temperature for thermally sensitive drugs, such as many proteins and polynucleotides.

In one embodiment, the polymer/drug matrix is formed by directing, for example, by pouring, atomizing, spraying or dripping, the polymer solution/drug mixture into a gas, which can be a liquified gas, which is at a temperature sufficient to freeze the polymer solution/drug mixture, forming solid polymer solution/drug mixture particles. The solvent can then be removed from these particles by, for example, contacting the particles with a nonsolvent at a temperature below the freezing point of the particles, whereby the solvent is extracted into the nonsolvent, or by lyophilizing the particles in vacuo.

In another embodiment, the polymer solution/drug mixture is directed into a nonsolvent, for example, ethanol or isopentane, at a temperature above the freezing point of the polymer/drug mixture, but still sufficiently low to cause precipitation of the polymer/drug matrix. This yields a nonsolvent/polymer/drug matrix mixture, from which the polymer/drug matrix can be removed by filtration.

In a preferred embodiment, the polymer/drug matrix is formed by directing, for example, by pouring, atomizing, spraying or dripping, the polymer solution/drug mixture into a liquid nonsolvent, such as an alcohol, for example, ethanol, or a nonpolar organic liquid, such as an alkane, at a temperature below the freezing point of the polymer solution/drug mixture, thereby forming a solid polymer solution/drug mixture. This is followed by extraction of the solvent from the solid polymer solution/drug mixture into the nonsolvent, yielding a polymer/drug matrix.

In a further embodiment, the solid polymer/drug matrix can be formed by extruding the polymer solution/drug mixture as a continuous liquid stream, for example, through a syringe, into a liquid nonsolvent or a nonsolvent overlaid with a liquified gas, at a temperature below the freezing point of the polymer solution/drug mixture. This yields a solid polymer solution/drug mixture, from which solvent is extracted into the nonsolvent. Alternatively, the polymer solution/drug mixture can be extruded into a gas at a temperature suitable for freezing the mixture. The solvent is then removed from the resulting solid polymer solution/drug mixture by, for example, contacting the solid mixture with a nonsolvent at a temperature below the freezing point of the mixture, whereby the solvent is extracted into the nonsolvent, or by lyophilization of the solid mixture.

After removal of the solvent and/or nonsolvent from the solid polymer/drug matrix, the matrix is fragmented to produce particles of a size suitable for injection. In one embodiment the target size range is from about 30 $\mu$m to about 180 $\mu$m. The fragmentation is performed at a temperature below the glass transition temperature of the polymer/drug matrix; below this temperature the matrix is brittle. For example, the temperature of the fragmentation step can be less than about 40° C., preferably less than about 4° C. Fragmentation methods include grinding, milling, homogenization, or pulverization methods which can be performed at low temperature. For example, the solid matrix can be fragmented at low temperature using an analytical mill with a cryogenic attachment, or crushed with a pestle while held under liquid nitrogen in a mortar, or in an environment which is at a temperature below the glass transition temperature of the polymer. The matrix can be dry when fragmented, or it can be suspended in a nonsolvent at a temperature below its glass transition temperature.

The size range of the polymer/drug matrix microparticles prepared by the present method can be controlled in the fragmentation step. In the embodiment of the method described in Example 1, the final particle size distribution is a function of the total grinding time, with shorter grinding times producing, on average, larger particles, and longer grinding times producing, on average, smaller particles. The size range of a sample of microparticles produced in this way can be further restricted by sieving, thus eliminating particles outside a specified size range.

Polymers which can be used in the formulation of polymer/drug matrix microparticles include any polymer which is biocompatible. A biocompatible polymer and its degradation products are non-toxic toward the recipient. These include bioerodable polymers such as poly(lactic acid), poly(glycolic acid), poly(lactide), poly(glycolide), poly(lactide-co-glycolide)s, poly(caprolactone), polycarbonates, polyamides, polyanhydrides, poly(amino acid)s, poly(ortho ester)s, polyacetals, polycyanoacrylates, poly(ether ester)s, poly(dioxanone)s, poly(alkylene alkylate)s, copolymers of poly(ethylene glycol) and poly (ortho ester), degradable polyurethanes and copolymers and blends thereof. Also included are non-bioerodable polymers such as polyacrylates, ethylene-vinyl acetate copolymers, acyl-substituted cellulose acetates, non-degradable polyurethanes, polystyrenes, polyvinyl chloride, polyvinyl fluoride, poly(vinylimidazole), chlorosulfonate polyolefins, and polyethylene oxide. Any suitable blends or copolymers of these materials can also be used. Solvent/nonsolvent systems suitable for a given polymer can be determined via routine experimentation.

In a particularly preferred embodiment of the present method, the polymer used is a poly(lactic acid-co-glycolic acid) (d,l-PLGA) copolymer. In this embodiment, suitable solvents for forming the polymer solution/drug mixture include methylene chloride, acetone, ethyl acetate, methyl acetate, tetrahydrofuran and chloroform. Suitable nonsolvents include alcohols, such as ethanol, and nonpolar hydrocarbon solvents, such as isopentane.

A further embodiment of the present invention includes the polymer/drug matrix microparticles which are produced by the method described above. These microparticles comprise a biocompatible polymer, a labile drug and, optionally, one or more excipients and/or a release modifier, such as a metal-containing salt. The particles can be homogeneous or heterogeneous. Microparticles produced from polymer solution/drug mixtures wherein the drug is co-dissolved can be homogeneous, with a uniform dispersion of drug molecules throughout the matrix. In certain cases, however, the drug molecules can aggregate upon freezing the polymer solution/drug mixture or upon removing the solvent from the mixture, resulting in a heterogeneous polymer/drug matrix. Those microparticles produced from polymer solution/drug mixtures wherein the drug is suspended will be heterogeneous, with regions of higher and lower drug density. These particles can have a wide range of sizes and are characterized by an irregular morphology. These polymer/drug matrix microparticles can have any extent of drug loading, as expressed by the weight percent of drug within the matrix. In a preferred embodiment, the drug loading is in the range of 0.01% to 50% of the total matrix weight.

A further aspect of the present invention is a method for forming an implantable polymer/drug matrix mass. In one embodiment, the method comprises the steps of (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) mechanically compressing the polymer/drug matrix, thereby forming an implantable polymer/drug matrix mass. Steps (1) and (2) can be performed as described above for the formation of polymer/drug matrix microparticles.

In another embodiment, the method further comprises the step of fragmenting the solid polymer/drug matrix at low temperature prior to compressing the solid polymer/drug matrix. This fragmentation can be accomplished according to the methods outlined above for the formation of polymer/drug matrix microparticles. In this embodiment, therefore, formation of the implantable mass comprises mechanically compressing drug/polymer matrix particles or microparticles.

This method is particularly advantageous when the drug is a labile drug, because the polymer/drug matrix is formed, as previously described, at low temperature and without requiring dissolution of the drug in an organic solvent, heat extrusion, melt pressing or the presence of an aqueous/organic interface.

The mechanical compression of the polymer/drug matrix can be accomplished in one of several ways. For example, a desired amount of polymer/drug matrix can be weighed out and compressed with a mechanical press. The resulting wafer can be implanted whole, or cut into smaller pieces to be implanted individually. The polymer/drug matrix can also be combined with a binding agent, such as bulk polymer or another biocompatible material, prior to compression. In one embodiment the bulk polymer is a polymer of different composition and properties (for example, with a lower glass transition temperature) than that in the polymer/drug matrix. In another embodiment, the polymer/drug matrix, or the polymer/drug matrix combined with a binding agent, can be compressed into a rod, and the rod can be implanted or injected through a large bore syringe. Alternatively, wafers of desired thickness can be sliced off the end of the rod and implanted.

The method of forming implantable devices can further comprise the step of heating the resulting implant transiently to at least the glass transition temperature of the polymer or the binding agent. This can be done to optimize the characteristics, such as resilience or surface morphology, of the final product. The compressed implant can also be coated with a biocompatible coating to improve handling characteristics or to modify release characteristics.

An advantage of the present method is that it enables the formation of implantable devices having very low residual solvent content, for example, less than about 50 parts per million residual solvent by weight. This is particularly true when the polymer solution/drug mixture is frozen prior to solvent removal.

A further aspect of the present invention includes an implantable polymer/drug matrix mass prepared by the present method. Such a polymer/drug matrix mass comprises a biocompatible polymer, and a drug dispersed within the polymer matrix as discussed above for a polymer/drug matrix microparticle. A polymer/drug matrix mass of the present invention can additionally comprise one or more excipients, release modifiers and/or additional drugs, as previously discussed for a polymer/drug matrix microparticle, as well as a binding agent. The polymer/drug matrix mass can also be coated with a biocompatible polymer. The polymer/drug matrix mass can be of any suitable form, such as a wafer, rod or bead.

The invention will now be further and specifically described by the following examples.

EXAMPLES

Example 1 Preparation of Polymer/Drug Matrix Microparticles

Preparation of Erythropoietin Formulation Suspension in Polymer Solution

Human erythropoietin (EPO) was derived as described in U.S. Pat. No. 4,703,008. The EPO was dissolved in deionized water to form an aqueous solution having a concentration of approximately 1 mg/mL. The EPO solution was then dialyzed against three changes of the formulation buffer, 5 mM phosphate buffer, pH 7.

Following dialysis, the concentration of EPO in the dialyzed solutions was verified to be approximately 1 mg/mL as determined by measuring absorbance at 280 nm ($\epsilon$=1.345 L g$^{-1}$ cm$^{-1}$). The dialyzed EPO solution was then mixed with a concentrated solution of ammonium sulfate and inulin. The ammonium sulfate solution was separately prepared in 5 mM phosphate buffer, pH 7. Appropriate volumes of the ammonium sulfate solution and of additional buffer were added to a 50 mL polypropylene tube to achieve the desired concentration for the formulation. The dialyzed EPO solution was then added to the solution and mixed by gentle inversion.

The formulated EPO solution was aspirated into a 60 mL plastic syringe fitted with teflon tubing and then atomized through an ultrasonic nozzle (Type VIA; Sonics and Materials, Inc., Danbury, Conn.) into a polypropylene container containing liquid nitrogen, making sure that the atomized material was fully submerged at all times, to form frozen particles. The container was kept at −80° C. until the liquid nitrogen was entirely evaporated. The frozen particles, which contained biologically active, aggregation-stabilized EPO, were transferred into a glass beaker, then lyophilized to form biologically active, aggregation-stabilized EPO particles. The EPO particles were removed from the lyophilizer under an atmosphere of dry nitrogen, handled in a low humidity environment, and stored dessicated at −80° C. The lyophilized EPO formulation comprised, by weight, 10% EPO, 79% ammonium sulfate, 10% phosphate salts, and 1% inulin.

A solution (10% w/v) of 10 kd unblocked D,L-PLGA was prepared in methylene chloride. The EPO particles (25 mg) and sieved magnesium carbonate (50 mg, less than 38 $\mu$m) were added to 4.25 mL of this solution. The resulting suspension was sonicated with an ultrasonic probe (Virtis Co., Gardner, N.Y.) for 30 seconds, in order to reduce the protein particle size.

Preparation of Polymer/Drug Matrix by Drop Freezing

The polymer/drug matrix was formed by allowing drops of the drug suspension in the polymer solution to fall, over a period of about one minute, from a 5 mL glass pipet into a bed of liquid nitrogen, which overlaid a frozen bed of ethanol (170 mL). The drop size was approximately 10–50 $\mu$L. The entire bath containing the particles was placed in a −80° C. freezer, where the nitrogen was allowed to evaporate. The ethanol bed subsequently melted, engulfing the polymer/drug matrix particles. The particles were allowed to cure to extract the methylene chloride. At 24 hours, an additional volume (170 mL) of ethanol, prechilled to −80° C., was added to the tub. After 48 hours, the particles were collected by filtration using a Buchner funnel in a nitrogen-purged glove box and dried in a lyophilizer. The particles produced by this method were of irregular shape and approximately 2 to 4 mm in diameter.

Preparation of the Polymer/Drug Matrix by Extrusion

A polymer/drug matrix was formed by extruding the drug suspension in the polymer solution through a glass syringe equipped with a stainless steel 22 gauge needle, into a frozen bed of ethanol overlaid with liquid nitrogen, as described above, over a period of several seconds. Subsequent steps were identical to those described above. The particles produced by this method were similar to those produced by drop-freezing.

Cryogenic Milling of the Polymer/Drug Matrix

The particles prepared via the methods described above were subjected to grinding in a mortar and pestle which was pre-chilled with liquid nitrogen. Care was taken to ensure that the particles were submerged in liquid nitrogen at all times. The particles were crushed with the pestle until they appeared to be uniformly small. Upon completion of the grinding step, the particles were transferred as a slurry in liquid nitrogen into a prechilled 20 mL glass vial. The vial was then placed in a −80° C. freezer. After evaporation of the nitrogen from the vial, the vial was transferred to a vacuum desiccator and the material was dried in vacuo at room temperature to remove any residual moisture from the particles. The particles were then sieved with a 250 $\mu$m sieve.

Example 2 In Vivo Characterization

Male Sprague-Dawley rats, weighing 400±50 g (S.D.), were used as the animal model. The rats were not fasted, before the experiments and subsequently were fed with a standard diet, an iron supplement, and allowed free access to water. Iron dextran (Sigma Co., St. Louis, Mo.) was injected intraperitoneally twice a week.

The response of the rats' immune systems to EPO was suppressed by administration of cyclosporin A and hydrocortisone to the test animal. Each rat was given daily an intraperitoneal injection of 10 mg cyclosporin A (Sandimmune® Injection, Sandoz, East Hanover, N.J.) and 5 mg hydrocortisone (Spectrum Co., Gardena, Calif.) in 0.5 mL sterilized saline for injection (USP) for days 0 to 14.

The rats were injected subcutaneously in the interscapular region at hour 0 with 10,000 units of EPO in the form of EPO/polymer matrix microparticles prepared as described in Example 1. Blood samples were taken from the tail vein of each rat at 3, 12, 24, 32, and 48 hours after injection. Additional blood samples were then taken approximately once a day for the following 10–12 days.

EPO concentrations in rat serum were determined by enzyme-linked immunosorbent assay (ELISA). The results, shown in FIG. 1, clearly show sustained release of EPO from the particles over a twelve day period. Serum profiles are normalized to a dose of 10,000 IU per animal.

For comparison, serum profiles of rats treated with the same formulation prepared by the method described by Gombotz et al. are included in the figure. There is no appreciable difference between the in vivo performance of microspheres prepared according to Gombotz et al. and the particles prepared as described in Example 1.

Example 3 In Vitro Characterization

Characterization of in vitro release properties of the polymer/EPO microparticles described in Example 1 was performed. Microparticles were suspended in HEPES buffer and the resulting suspension was maintained at 37° C. for 118 days. The extent of EPO release was determined by size exclusion chromatography. FIGS. 2 and 3 show the release profiles of PLGA/EPO microparticles prepared from a PLGA/EPO matrix formed by drop freezing (FIG. 2), or extrusion (FIG. 3). Less than 5% of total released protein was in aggregate (inactive) form.

Example 4 Preparation and Characterization of In Vivo Release From EPO/PLGA Matrix Implantable Devices

Preparation of Implantable Devices

PLGA implants containing encapsulated erythropoietin were prepared using mechanical compression of EPO/PLGA microspheres prepared by the method of Gombotz et al., U.S. Pat. No. 5,019,400, and of microparticles prepared using the method of Example 1 above.

EPO/PLGA matrix wafers were formed by compression of the EPO/PLGA microparticles or microspheres in a Carver Laboratory Press (Model C; Fred S. Carver Inc., Menomenee Falls, Wis.). To a ½" diameter stainless steel test cylinder outfit, 100 mg of material were added. Wafers were formed at 15,000 psi for 15 seconds, and cut into smaller pieces as needed using a razor blade. Wafer fragments were weighed prior to implantation to determine the dose administered.

The devices prepared and tested are summarized in the following table (SC: subcutaneous):

| Device | Method of Fabrication | Method of Administration |
| --- | --- | --- |
| A. Microspheres | U.S. Pat. No. 5,019,400 (Gombotz, et al.) | SC injection as a suspension in vehicle[1] |
| B. Wafer | Compression of an intimate mixture of lyophilizate, bulk polymer, and release modifier (in the absence of solvent)[2] | SC Implantation |
| C. Wafer | Compression of microspheres prepared according to U.S. Pat. No. 5,019,400 (Device A) | SC Implantation |
| D. Wafer | Compression of polymer/drug matrix prepared according to Example 1 (using drop freezing) | SC Implantation |

[1] Vehicle composition: 1% glycerol/0.9% NaCl, 0.5% gelatin/2% CMC (LV).
[2] Disclosed by J. D. Gresser and J. E. Sanderson, Biopolymeric Controlled Release System Vol II., p. 136 (CRC Press, 1984).

In Vivo Characterization

Dry wafers were inserted subcutaneously into an incision made in the mid scapula region (after shaving and disinfecting the site) of Sprague-Dawley rats. Incisions were closed with staples and surgical glue. The kinetics of release of EPO from the depot formulations were assessed by monitoring serum EPO levels with immuno-suppression as described in Example 2.

Figure 4:
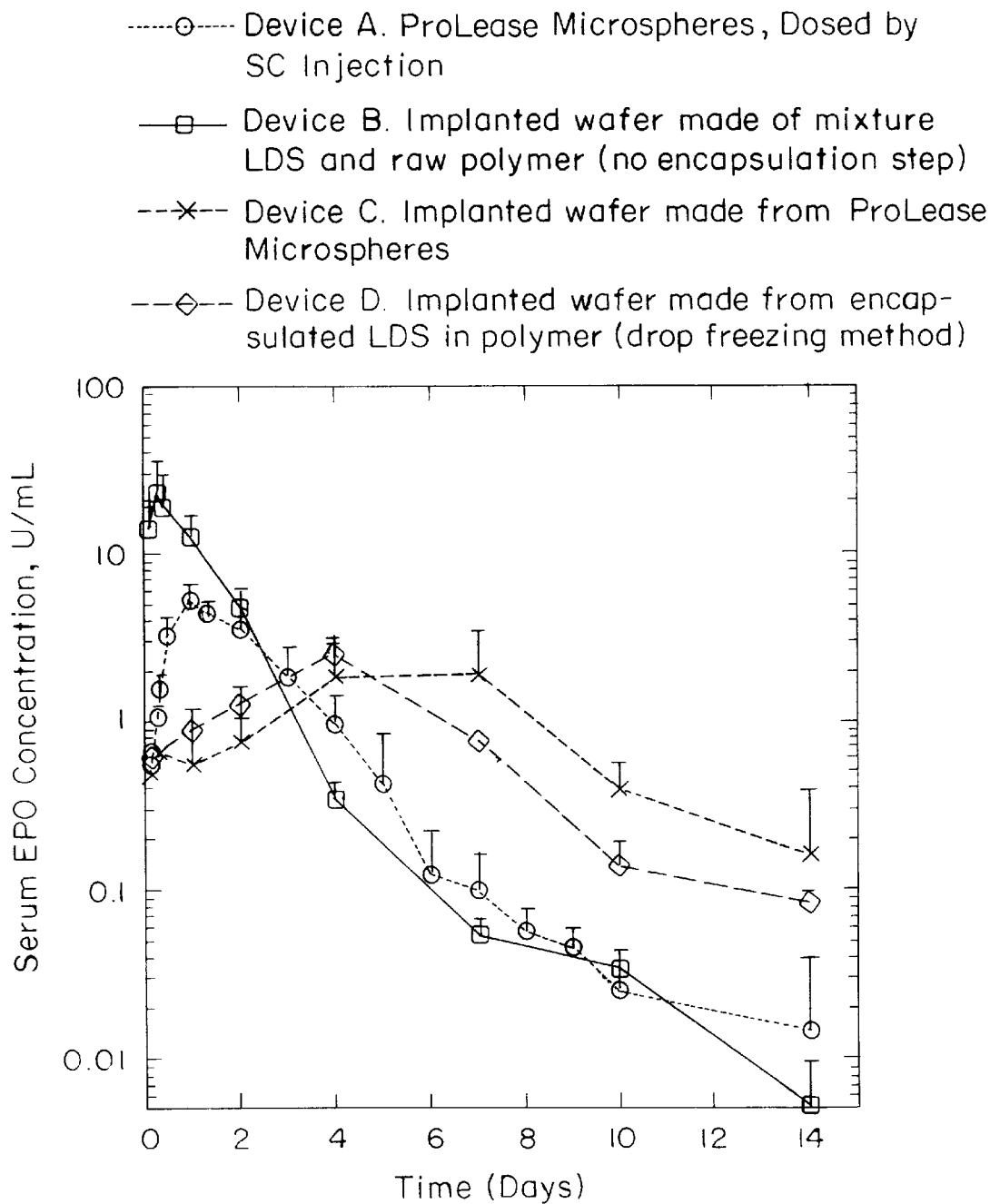
FIG. 4 is a graph comparing in vivo release in rats of erythropoietin for four different EPO/PLGA matrix continuous release devices: microspheres produced according to the method of Gombotz et al.; a wafer prepared by the compression of microspheres prepared according to the method of Gombotz et al.; a wafer prepared by compression of microparticles of the present invention; and a wafer prepared by compression of a solid state mixture of PLGA and EPO drug substance.

The results obtained with the four devices listed in the table above are shown in FIG. 4. In all four cases, the serum EPO level after day 14 was below the quantitation level for the ELISA assay, indicating that the duration of release was the same for all-four devices. However, the kinetics of release of EPO, inferred from the serum EPO levels, differed dramatically among the four devices. The duration of release of EPO was the same for the implants as for the injected microspheres. However, in the crucial second half of the release period, the implants produced serum EPO levels approximately ten-fold higher than those observed with the microspheres.

Equivalents

Those skilled in the art will recognize or be able to ascertain using no more than routine experimentation many equivalents to the specific embodiments of the invention described herein. Such equivalents are intended to be encompassed in the scope of the following claims.

What is claimed is:

1. A method for forming non-spherical polymer/drug matrix microparticles of irregular shape, wherein the drug is a labile drug, comprising a sequence of steps consisting essentially of the steps of:
   (a) forming a polymer solution/drug mixture comprising a polymer dissolved in an organic solvent and a suspended drug which is substantially insoluble in the organic solvent;
   (b) removing the solvent from the polymer solution/drug mixture, thereby forming a solid polymer/drug matrix; and
   (c) fragmenting the polymer/drug matrix by pulverizing, grinding or milling said matrix at a temperature below the glass transition temperature of the polymer/drug matrix, thereby forming non-spherical polymer/drug matrix microparticles.

2. The method of claim 1 wherein the labile drug is a therapeutic, diagnostic or prophylactic agent.

3. The method of claim 2 wherein the labile drug is an immunoglobulin protein, an antibody, a cytokine, an interleukin, an interferon, erythropoietin, a nuclease, tumor necrosis factor, a colony stimulating factor, insulin, an enzyme, a tumor suppressor, a hormone, an antigen, a growth factor, a peptide, a polypeptide, or a polynucleotide.

4. The method of claim 2 wherein the labile drug is a protein.

5. The method of claim 1 wherein the polymer/drug matrix is fragmented while in contact with a nonsolvent.

6. The method of claim 1 wherein the polymer/drug matrix is fragmented by milling the polymer/drug matrix in an analytical mill.

7. The method of claim 1 wherein the polymer/drug matrix is fragmented by pulverizing the polymer/drug matrix with a mortar.

8. The method of claim 1 wherein the solvent is removed from the polymer solution/drug mixture at a temperature below the freezing point of the polymer solution/drug mixture.

9. The method of claim 1 wherein the organic solvent is dichloromethane, acetone, ethyl acetate, tetrahydrofuran, or methyl acetate.

10. The method of claim 1 wherein the polymer is a bioerodable polymer.

11. The method of claim 10 wherein the bioerodable polymer is selected from the group consisting of poly(lactic acid), poly(lactic acid-co-glycolic acid) copolymer, poly (caprolactone), polycarbonates, polyamides, polyanhydrides, poly(amino acid)s, poly(ortho ester)s, polyacetals, polycyanoacrylates and polyurethanes.

12. The method of claim 10 wherein the polymer is a copolymer or a polymer blend.

13. The method of claim 1 wherein the drug is suspended as a powder.

14. The method of claim 1 wherein the polymer solution/drug mixture further comprises one or more excipients.

15. The method of claim 14 wherein the excipients are selected from the group consisting of surfactants, acids, bases, sugars, and stabilizers.

16. The method of claim 1 wherein the polymer solution/drug mixture further comprises one or more additional drug substances.

17. The method of claim 1 wherein the polymer solution/drug mixture further comprises a release modifying agent.

18. The method of claim 17 wherein the release modifying agent is a metal-containing salt.

19. The method of claim 1 wherein the solvent is removed from the polymer solution/drug mixture by a method comprising the steps of:

(i) freezing the polymer solution/drug mixture, thereby forming a solid polymer solution/drug mixture; and (ii) extracting the solvent from the solid polymer solution/drug mixture.

20. The method of claim 19 wherein the solvent is extracted from the polymer solution/drug mixture by contacting the solid polymer solution/drug mixture with a nonsolvent, thereby extracting the solvent into the nonsolvent.

21. The method of claim 19 wherein the solvent is extracted from the solid polymer solution/drug mixture by lyophilizing the solid polymer solution/drug mixture.

22. The method of claim 19 wherein the polymer solution/drug matrix is frozen by directing the polymer solution/drug mixture into a liquid nonsolvent, at a temperature below the freezing point of the polymer solution/drug mixture.

23. The method of claim 22 wherein the polymer solution/drug mixture is directed into the liquid nonsolvent by pouring, atomizing, spraying, extruding or dripping the polymer solution/drug mixture into the liquid nonsolvent.

24. The method of claim 19 wherein the polymer/drug matrix is frozen by directing the polymer solution/drug mixture onto a frozen nonsolvent bed in the presence of a liquified gas.

25. The method of claim 24 wherein the gas is dinitrogen or argon.

26. The method of claim 24 wherein the polymer solution/drug mixture is directed onto the frozen nonsolvent bed in the presence of a liquified gas by pouring, atomizing, spraying, extruding or dripping the polymer solution/drug mixture onto the frozen nonsolvent bed.

27. The method of claim 19 wherein the polymer solution/drug mixture is frozen by extruding the polymer solution/drug mixture into a gas at a temperature suitable for freezing the polymer solution/drug mixture.

28. The method of claim 1 wherein the solvent is removed from the polymer solution/drug mixture by a method comprising the steps of:

(i) directing the polymer solution/drug mixture into a nonsolvent at a temperature suitable for precipitating the polymer/protein matrix, thereby forming a polymer/drug matrix-nonsolvent mixture; and (ii) separating the nonsolvent and the polymer/drug matrix by filtering the polymer/drug matrix-nonsolvent mixture.

29. The method of claim 28 wherein the nonsolvent is ethanol or isopentane.

30. The method of claim 28 wherein the polymer solution/drug mixture is directed into the nonsolvent by pouring, atomizing, spraying, extruding or dripping the polymer solution/drug mixture into the solvent.

31. The method of claim 1 wherein the solvent is removed from the polymer solution/drug mixture by evaporating the solvent.

32. The method of claim 31 wherein the polymer solution/drug mixture is spread in a film prior to evaporating the solvent.

33. The method of claim 31 wherein the polymer solution/drug mixture is sprayed onto a surface prior to evaporating the solvent.

* * * * *